United States Patent [19]
Proni

[11] Patent Number: 5,221,272
[45] Date of Patent: Jun. 22, 1993

[54] UNIFIED MEDICAL FLUID SYSTEM

[75] Inventor: Oscar Proni, Hollywood, Fla.

[73] Assignee: Safegrip, Inc., Miami, Fla.

[21] Appl. No.: 801,246

[22] Filed: Dec. 3, 1991

[51] Int. Cl.⁵ ............................................. A61M 25/00
[52] U.S. Cl. ................................... 604/283; 604/183; 604/240
[58] Field of Search ............................... 604/283–284, 604/905, 411–414, 240–245, 205

[56] References Cited

U.S. PATENT DOCUMENTS

| | | | |
|---|---|---|---|
| 1,529,659 | 3/1925 | Marcy | 604/243 |
| 4,123,091 | 10/1978 | Consentino et al. | 604/240 |
| 4,511,359 | 4/1985 | Vaillancourt | 604/905 |
| 4,981,469 | 1/1991 | Whitehouse et al. | 604/905 |
| 4,998,713 | 3/1991 | Vaillancourt | 604/905 |
| 5,088,984 | 2/1992 | Fields | 604/905 |
| 5,120,324 | 6/1992 | Sancoff | 604/243 |

*Primary Examiner*—C. Fred Rosenbaum
*Assistant Examiner*—Manuel Mendez
*Attorney, Agent, or Firm*—Fish & Richardson

[57] ABSTRACT

A quick connect fluid coupling assembly serving as the basic building block in a unified system for fluid transmission for use in the medical and health care fields provides a safety mechanical structure for prevention against pricking from a needle or other central fluid flow conduit, while also maintaining the mechanical features of the connector separate from the fluid channel. The sharp pointed central channel of the male connector component punctures a latex diaphragm of the complimentary female connector component, with a simple push inward of the female connector component enabling the locking connection. The connection remains secure since it is the slight change of shape in the deformable material during insertion that is removed once the connection is made, at which time a completely encircling shoulder rim bars any inadvertent disconnection.

11 Claims, 7 Drawing Sheets

UNIFIED MEDICAL FLUID SYSTEM

FIELD OF THE INVENTION

The invention relates to a unified system for delivering fluids to and extracting fluids from the human body. Each system component is joined by a reusable quick-connect, quick-disconnect coupling device incorporating a novel mechanical locking and release means. In this unified system both the health care provider, e.g., physician, nurse, etc., and the patient are protected at every juncture within the system from exposure to needles or other sharp objects. Each juncture results in a positive mechanical lock, as opposed, for example, to a frictional fit, and a protected, enclosed fluid transfer means. Specifically, this invention relates to quick-connect couplers primarily for use in the medical field and, more particularly, to a coupling incorporating a fluid transfer means, such as needle-like structures.

BACKGROUND OF THE INVENTION

Figure 12:
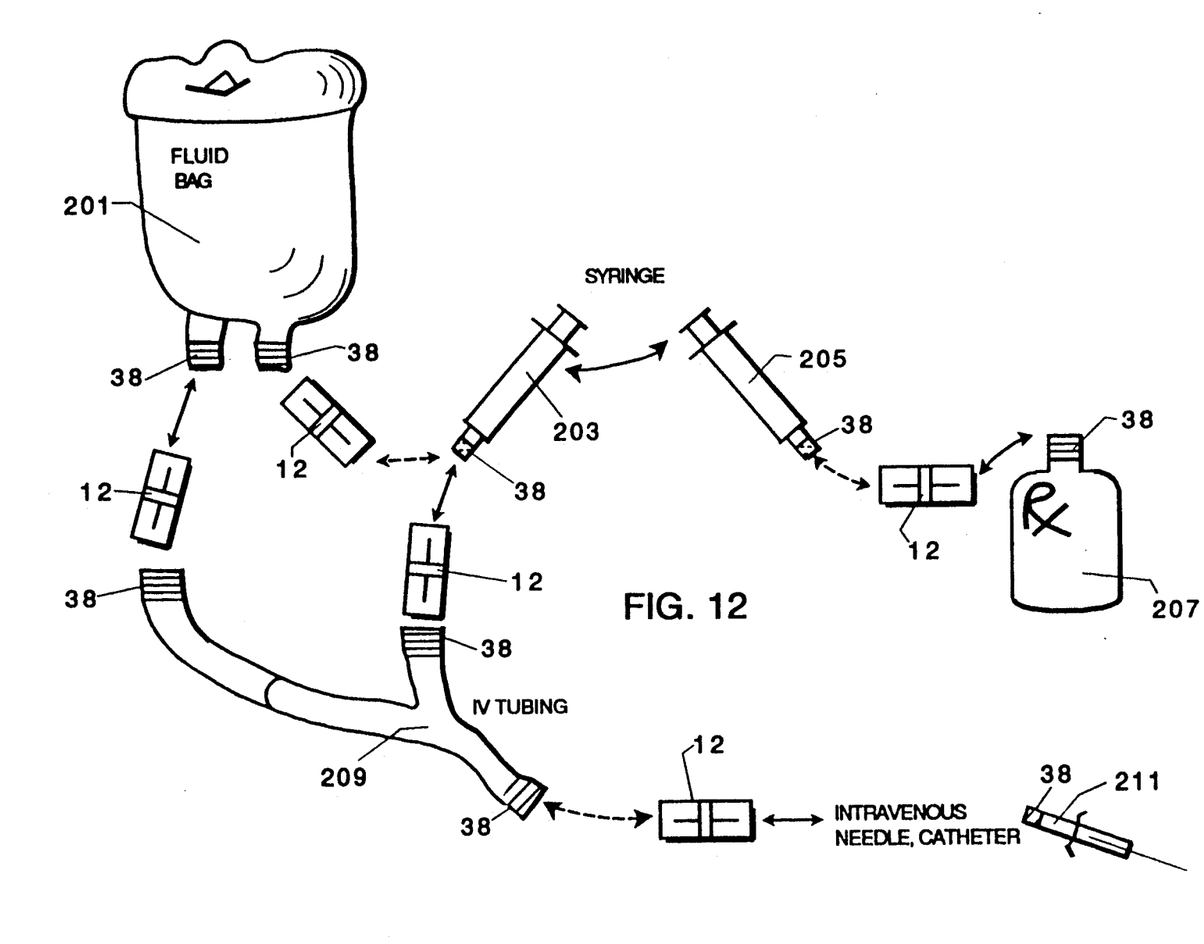
FIG. 12 illustrates a medical interconnection system utilizing the connector of the invention in a universal connection system.

Delivering fluids to and extracting fluids from the human body is a basic part of the physicians task in the treatment of patients. Fluids delivered include a variety of solutions, and fluids removed include human blood. FIG. twelve illustrates typical components of a fluid delivery or extraction system; some of these components include an intravenous solution bag (I.V. bag) or bottle container, a syringe, medication bottle, nasogastric tube, a urethral catheter, tubing, etc. To interact with and utilize these components the physician is often exposed to unprotected needles. Furthermore, the interconnections among devices often disconnect, spilling contaminated fluids upon patients, health care personnel, and hospital equipment. A great deal of time is consumed in making often unreliable connections among fluid transport systems. The couplings presented in the present invention overcome the difficulties of the prior art and permit the construction of a unified system, e.g., a system where all components are joined with the same universal couplers.

Quick connect assemblies have been known in the prior art for many years. Areas in which quick-connect couplings have been applied include hydraulics, pneumatics, plumbing, and so on. Such connector assemblies, while widely used in areas such as industrial tubing connectors and electrical connectors, have had limited successful application to areas involving fluid delivery for medical or health care purposes. Few of the prior art quick-connect, fluid flow couplings have successfully incorporated needle or needle-like structures within the internal structure of the coupling in such a way that keeps the fluid flow apart from the mechanical coupling, while also giving full protection to the user against accidental pricking by the needle or other needle-like structure.

In the delivery of fluids in medical systems in common use today, e.g., in intravenous anti-biotic delivery systems, needles are common components of the fluid delivery apparatus, and the accidental disconnection of a needle forming the fluid connection is unfortunately all too common. Such accidental disconnections present safety hazards to staff personnel and threat of infections to the patient, particularly in a time of the emergence of diseases such as AIDS which carry fatal consequences with a slip of the wrong needle. An ever growing larger quantity of used needles must now be disposed of, again generating health hazards to hospital staff personnel and others involved in waste handling.

At present, the most commonly used connector appears to be the Luer lock which requires a turning or screwing motion in the application for mechanical locking and involves tapered internal surfaces for liquid sealing. The Luer Lock design is not the only connector design used in the medical area requiring rotational or screw actions for locking. The various connector designs in U.S. Pat. No. 4,668,217 to Isono, for example, all require a rotational action for connection.

More recently there has appeared in the patent literature a series of devices containing protected diaphragm or septum piercing, needle-like structures having quick-connect locks or quick-connect locks in combination with rotational locks. In U.S. Pat. No. 4,759,756 to Fonnan et. al., a "reconstitution device" is presented containing a protected needle structure and using a rotational split-jaw locking device in combination with a multiple-jaw or finger snap-gripping device. In U.S. Pat. No. 4,950,260 to Bonaldo for a "medical connector" a device is presented containing a protected needle structure using a locking cap, which is flipped into position for locking, in combination with a luer lock. In U.S. Pat. No. 4,927,423 to Malmborg, protected needle-like piercing members are used in combination with snap-lock circular beads within circular chambers for joining other chambers filled with liquids. In U.S. Pat. No. 4,998,927 to Vaillancourt a protected needle-like structure is used to pierce a septum using a flexible structure and is joined to external elements via luer lock structures.

In U.S. Pat. No. 5,037,405 to Crosby a protected needle is enclosed after connection within a hinged compartment which is then locked using a clasp mechanism. For U.S. Pat. No. 4,998,925 a protected needle is enclosed within a sleeve which is joined via frictional fits at both ends to other fluid system members. In U.S. Pat. No. 4,998,713 to Vaillancourt a protected needle is used within a Y connector using a cam-action lock mechanism. In U.S. Pat. No. 4,981,469 to Whitehouse et al. a protected needle structure is contained within an assembly joined via luer locks.

A number of locking mechanisms are available which are now being adapted for enclosed needle protection. In U.S. Pat. No. 4,969,879 an "alligator clip" mechanism, long familiar to those working in the electronics area, is used to join a stepped, tapered nozzle to a receptacle for said stepped, tapered nozzle. this alligator clip mechanism is now being used to join a protected needle structure for fluid connections. Some companies using the alligator clip concept include Block Medical, Inc. and Baxter Healthcare Corporation in such devices as "protective needle locks". Recently the Baxter Corporation has introduced an alligator clip device called a "Needle Less Cannula." This device is small but has the drawbacks of requiring significant squeezing force to open the alligator clips to make the fluid flow connection and a tendency for the device to slip from the hand. None has been fully satisfactory in meeting the needs in this field.

For example, one problem is the delay incurred during diagnosis and/or therapy because of the reoccurring need for an exact fitting. In an emergency situation, all to frequently only the wrong sizes for connecting pieces or pieces having non-complimentary systems to execute the connection, are found. For example, a friction fitting Toomey syringe may be needed to inject solution into a patient, and only a Luer locking syringe is available. Lack of a standardized or universal connector, particularly in the medical field where off times under emergency situations, a variety of different components must be connected/disconnected bother quickly and securely.

Another problem experienced with known types of connectors is the lack of separation between the fluid flow from the mechanical connection. Fluids coming in contact with the connection itself, over time, will cause difficulty in operation of the connection. For example, one problem experienced in medical emergency rooms is that the fluids, e.g., blood, cause difficulty in quickly disengaging two connector components. This could be particularly crucial in procedures such as a heart operation involving use of a cardiac catheter, where the operation of its Luer lock has been adversely affected by the fluid flow itself, by either being unable to smoothly separate, producing additive problems in trying to get a grip on delicate tubing, for example, or the opposite problem, in having the connector fall apart, an enhanced possibility with the use of friction fittings.

The following only briefly illustrates some of the disastrous consequences that originate from such a faulty medical connector: unexpected loss of blood could occur from a patient. A loss of medication or food being fed into a patient could be interrupted, with the fluids spewing onto the bed or floor. Unanticipated interruption of a medical fluid could cause contamination of the patient and/or the health care worker. When a connector is used for the flow of a gaseous fluid, such as oxygen, the friction connectors now most prevalent always present the possibility of separation, resulting in no oxygen or inadequate oxygen to the patient. When critical body measurements are taking place, such as by means of a bladder catheter tube, inadvertent connector separation results in inaccurate measurement of body fluids and an open source for urinary track infections. When the connector is used with a surgical drainage table, for example, should the connector fall apart, immediate contamination is possible again of both the patient and the health care personnel.

Medical connectors, while useful in certain situations, have not been able to overcome these disadvantages, and thus their usefulness has thus been limited.

The connector quick-connect, quick-disconnect mechanical locking system described herein can, of course, be applied to medical devices other than the connectors. A catheter insertion device can be made utilizing the mechanical principles described herein. Such device consists of a two-spring loaded cylinder whereupon an initial squeeze, the first spring is released driving the catheter into the patient. Upon a second squeeze the central stiletto or trochar contained within the catheter is removed and a female port ready to receive the male connector of the present invention is established.

SUMMARY OF THE INVENTION

The present invention overcomes the disadvantages of the conventional connectors presently available. Therefore, it is an object of the invention to provide a reusable fluid quick-connect coupling assembly requiring a simple push for insertion, sealing, and locking and a very slight squeeze for unlocking and removal so to minimize the exposure of users to potentially dangerous structures capable of puncturing the human skin and to thereby avoid the deficiencies of prior art couplings. Another object of the invention is to provide a universal system for a quick yet secure fluid flow connection between various different components as are frequently required to be interconnected, for example, during an operation procedure. Such a universal system would have the components prefitted from their respective manufacturer with a female component of the inventive connector. The male, double sided connector of the invention then provides the connection means for accomplishing the fluid flow in a sterilized environment, separate from the mechanics of the connector's locking mechanism.

These and other objects of the invention are provided by a quick connect fluid coupling assembly comprising a primary body including a centrally disposed elongated channel extending therethrough coaxially to be longitudinal axis thereof, a non-flexible central portion, a flexible retaining portion and a portion integrally joining said non-flexible portion to said flexible portion; and a diaphragm piercing, sharp-tipped, cylindrically shaped hollow needle incorporated within and coaxial to the longitudinal axis of the primary body having the exterior surface of the needle integrally attached to the surface of the non-flexible portion of the primary body and extending longitudinally beyond the non-flexible portion a sufficient length so as to terminate within the flexible portion of the primary body; and a conduit removably disposed within the centrally disposed elongated channel and passageway, having a diaphragm covered end disposed on the interior of the primary body and forming a fluid-tight sealing engagement with the diaphragm piercing needle when the conduit is positioned along the length and locked in the channel.

Preferably, the conduit of the quick connect assembly comprises a distal end on the same longitudinal axis as the interior wall surface and opposite therefrom having connect means for connecting the distal end to a fluid source.

Preferably also, the flexible portion of the quick connect assembly forms an elliptically shaped ring for receiving the conduit along the longitudinal axis, and is adaptable to changing to more of a circular shape upon receipt of external forces directed radially inward for removal of the conduit from the elongated channel.

Another feature is a quick connect assembly wherein the flexible portion comprises a ring integrally connected with, and at essentially right angles to, the portion integrally joining or connecting the flexible portion of the connector assembly to the non-flexible portion of the connector assembly.

Preferably also, the flexible portion of the quick connect assembly has a joining or connecting portion comprised of two rigid sections positioned opposite to one another and separated by two spaces, each of the two rigid sections having a first end integrally connected to said central portion and extending outwardly therefore at essentially a right angle thereto, and a second end integrally attached to the flexible retaining portion.

Preferably also, the quick connect assembly has connect means that comprises a T-connector attachment; or connect means that comprises a Y-connector attachment; or has connect means integrally formed with a syringe.

According to another aspect of the invention, a quick connect fluid coupling assembly comprises a rigid central portion, a flexible retaining portion comprising stop means, and a connecting portion integrally joining the rigid central portion and the flexible portion to form a centrally disposed elongated channel extending coaxially through the primary body; a cylindrically shaped, diaphragm piercing hollow needle is disposed within the elongated channel and is coaxial to the longitudinal axis of the primary body, and comprises a first end of the needle integrally attached to the rigid central portion, and an opposite sharp-tipped end of the needle extending longitudinally outward from the rigid portion a sufficient length to terminate within the flexible portion of the primary body; a conduit removably insertable through the flexible retaining portion into the centrally disposed elongated channel, the conduit comprising an interior wall surface on which is disposed a diaphragm for forming a fluid-tight sealing engagement with the diaphragm piercing needle when the conduit is inserted along the length of said longitudinal axis and into the elongated channel; and lock means for securing the conduit in the elongated channel by engagement of the conduit with the stop means.

Other objects, features and advantages of our invention will be apparent from the following detailed description of preferred embodiments of the invention, taken together with the accompanying drawings wherein:

DESCRIPTION OF THE PREFERRED EMBODIMENT

Figure 1:
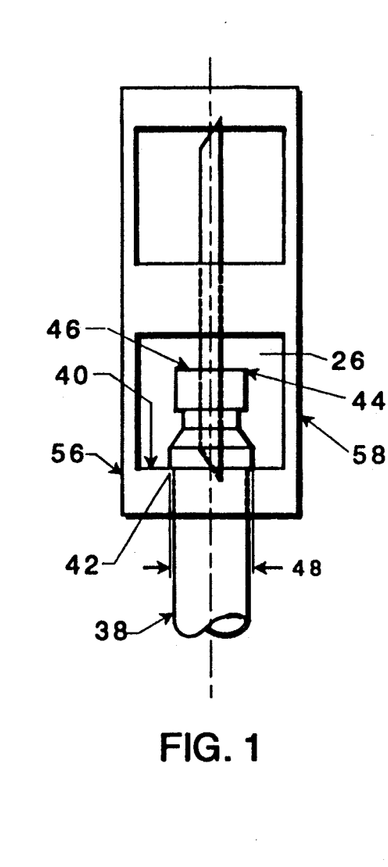
FIG. 1 illustrates a connector according to the invention.
Figure 2:
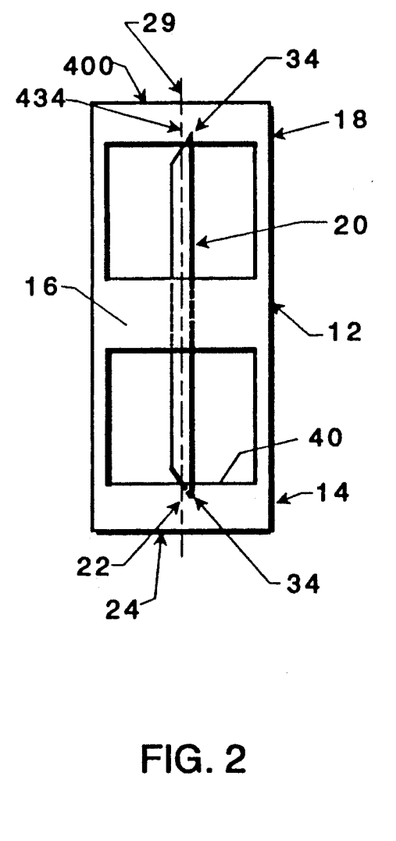
FIG. 2 shows the connector of FIG. 1 in an unengaged position.

Referring to FIG. 1, the complete connector 10 is shown consisting of a primary body 12 in an engaged position with a conduit 38. FIG. 2 shows the primary body 12 of the connector by itself, without engagement With the conduit. With reference to both FIGS. 1 and 2, the primary body 12 of connector 10 is formed of a flexible retaining end portion 14, a non-flexible central portion 16, and an opposite end portion 18. A central hollow axial tubular structure 20, such as a needle, extends from a location 22 in proximity to the distal end 24 of flexible retaining end portion 14, through and along the longitudinal axis of primary body 12 to a location 434 in proximity to distal end 400 of flexible end portion 18. Tubular structure 20 is integral with the primary body at its central portion 16. An external wall 30 joins, supports and separates the flexible retaining end portion from the non-flexible central portion of the primary body by a fixed spacing distance, with two similar opposite openings 26 appearing in wall 30 as shown. Particular portions of wall 30 forming the connection between central portion 16 and end portion 14 are identified as side wall 56 and 58.

A similar and opposing end structure exists in opposite end portion 18 which is connected with, and spaced a fixed distance from, central portion 16 by the same external wall 30. External wall 30 at this end also has two similar opposite openings 28 formed out of the wall.

Tubular structure 20 contains a central axial passageway 32 running lengthwise through the tubular structure and suitable for the transmission of fluid. The two end segments of tubular structure 20 consist of sharp pointed ends 34 suitable for puncturing a diaphragm made of latex, or of other similar material.

Figure 3:
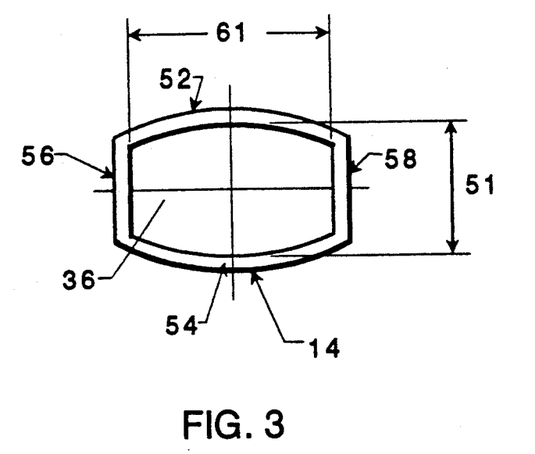
FIG. 3 presents a front face, end view of the connector.

FIG. 3 presents a frontal end view of the connector looking into retaining end portion 14 through which conduit 38 is inserted. It is seen that retaining end portion 14 includes two opposing long bowed walls 52, 54, integrally formed with two opposing short walls 56, 58. Together these walls define boundaries of a central axial channel 36 which forms the insertion and removal channel for conduit 38. Central channel 36 encompasses a sharp pointed end 34 of tubular structure 20 positioned at a location 22 in the central axial channel.

Retaining end portion 14 has an inside edge surface 40 that serves as one side of a boundary wall to openings 26 that are formed within external wall 30. On conduit 38 is an axially protruding stop member 42, spaced inwardly along the length of the conduit a sufficient distance from end 44 of conduit 38. End 44 is covered with a diaphragm 46.

A connection of conduit 3 to primary body 12 is made by inserting the conduit into the opening of central channel 36, with the following interaction occurring between the two components. Inside edge surface 40 of flexible end portion 14 cooperates with stop member 42 when the conduit is engaged into the primary body. The diaphragm 46 is pierced by sharp pointed end 34 when the conduit is inserted into central channel 36.

Stop member 42 may be in the form of an integrally formed outwardly extending annulatly configured ring or rim protruding a sufficient distance outwardly from the surface of conduit 38. The outer diameter 48 of the stop member is greater than the inside wall-to-wall distance 51 of the retaining end portion. However, due to the flexible nature of end portion 14, the stop member is able to pass through the central channel and inside of edge surface 40, as the following further describes.

Distance 51 between the internal surfaces of walls 52 and 54 is measured along a line perpendicular to the internal surfaces of those walls and passing through the central longitudinal axis 10 of primary body 12. As illustrated in FIG. 3, distance 51 is less than the distance 61 between the internal surfaces of wall 56 and 58.

Figure 4:
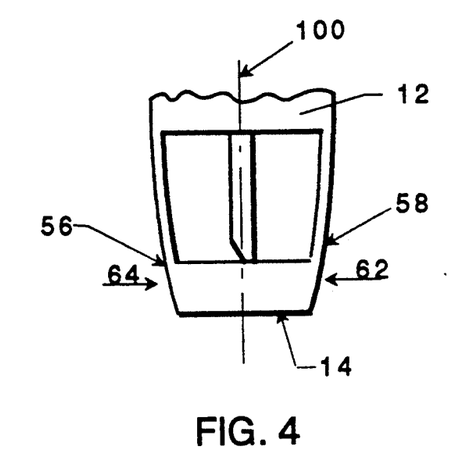
FIG. 4 illustrates the application of inwardly directed forces on the connector.

FIG. 4 depicts the application of radically inwardly directed external forces 62 and 64 applied to the exterior surfaces of walls 56 and 58, respectively. This causes a radially inward movement of these walls such that the distance 61 is reduced to a smaller distance 61'. Simultaneous with the inward movement of walls 56 and 58 under the application of forces 62 and 64, respectively, walls 52 and 54 move radially outward so that the distance 51 is increased to a larger distance, 51'. Forces 62, 64 may be applied, for example, by finger pressure of the user exerted about either side of the connector's primary body.

As a result of the application of forces 62 and 64, and the resulting radial inward movement of walls 56 and 58 together with the outward movement of walls 52 and 54, the distance 51' equals or exceeds the largest outer diameter 48 of stop member 42.

Figure 6:
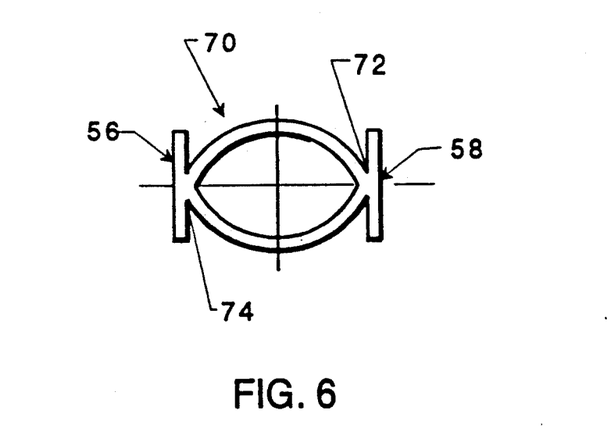
FIG. 6 is a second embodiment of the connector with an elliptical retaining end.

Looking next at FIG. 6 there is illustrated a second embodiment of the connector, wherein the flexible retaining end portion 14 is elliptical in shape when viewed in a frontal end view direction. Walls 56 and 58 integrally join elliptically shaped sections 70 at locations 72 and 74 respectively.

Figure 7:
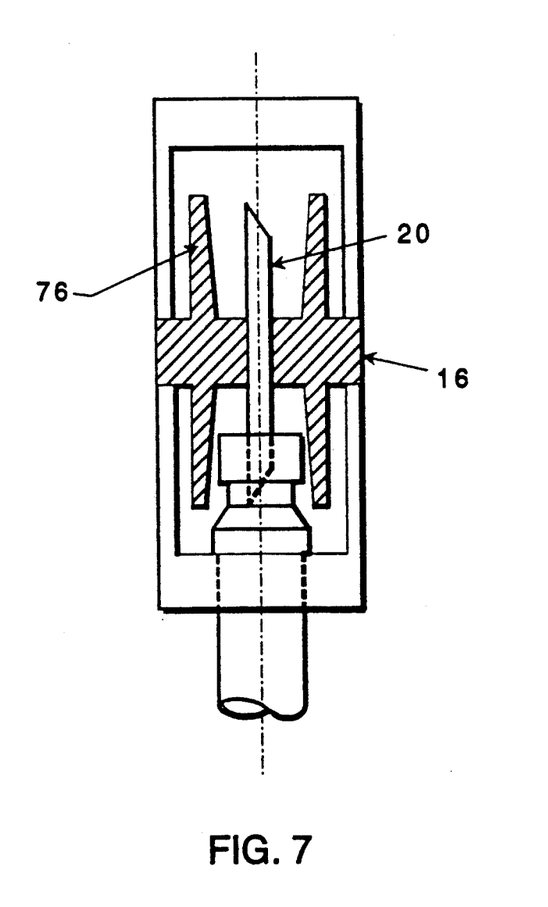
FIG. 7 illustrates a second embodiment of the connector according to the invention.

FIG. 7 presents a third embodiment of the connector where primary body 12 includes a rigid guide structure 76. The guides for receiving the conduit in this embodiment are made up of the tubular structure 20 which also provides the fluid flow conduit, and on either side thereof, a rigid guide structure 76 in the form of protruding fingers, essentially parallel to tubular structure 20. Rigid guide structure 76 is both co-axial with, and integral to, rigid central portion 16 of the connector.

The relative positions of retaining member 14 and conduit 38 prior to, during, and after the insertion of conduit 38 into the primary body of the connector are next illustrated and explained with reference to FIGS. 8, 9 and 10, respectively.

Figure 8:
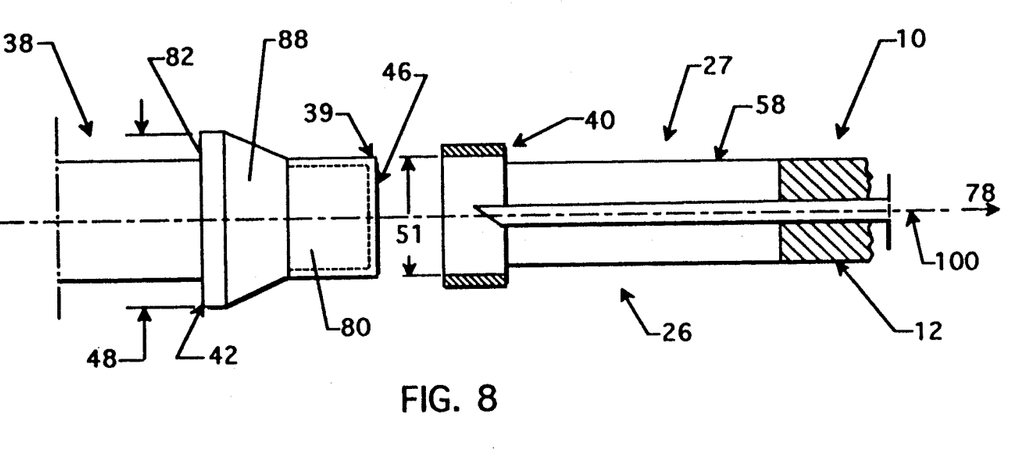
FIG. 8 shows the relative condition of the retaining member and the conduit prior to insertion of the conduit into the connector body.

In FIG. 8, connector 10 and conduit 38 are shown prior to insertion. Conduit 38 is pushed in a direction 78 and inserted into connector 10 with the central axis 80 of conduit 38 coinciding with the central axis 100 of connector 10. End 44 of conduit 38 is covered with a diaphragm 46 as a fluid sealant.

Figure 9:
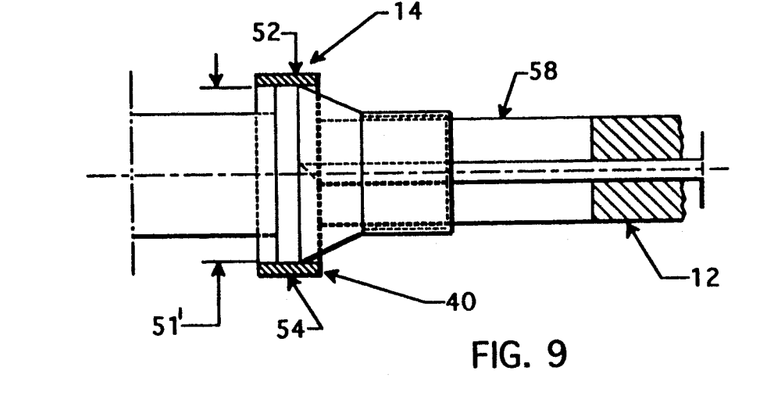
FIG. 9 shows the relative condition of the retaining member and the conduit during insertion of the conduit into the connector body.

FIG. 9 illustrates the two connector components during insertion where forces 64 and 62 are exerted upon walls 56 and 58, respectively, and walls 52 and 54 react by moving outward, such that the distance of interwall separation has increased from 51 to 51'. The distance 51' slightly exceeds the maximum diameter 48 of stop member 42, thereby permitting the stop member to pass through flexible retaining end portion 14 As the leading edge 39 of conduit 38 enters into flexible retaining end portion 14 and encounters the sharp pointed end 34 of tubular structure 20, diaphragm 46 covering the leading edge of the conduit is pierced. As conduit 38 continues to be pushed in a direction 78 and into primary body 12, the trailing edge 82 of stop member 42 passes surface edge 40 of flexible retaining end portion 14 of the connector. When this occurs, forces 62 and 64 are removed and end portion 14 returns to the condition and shape as initially indicated in FIG. 8, prior to insertion.

Figure 10:
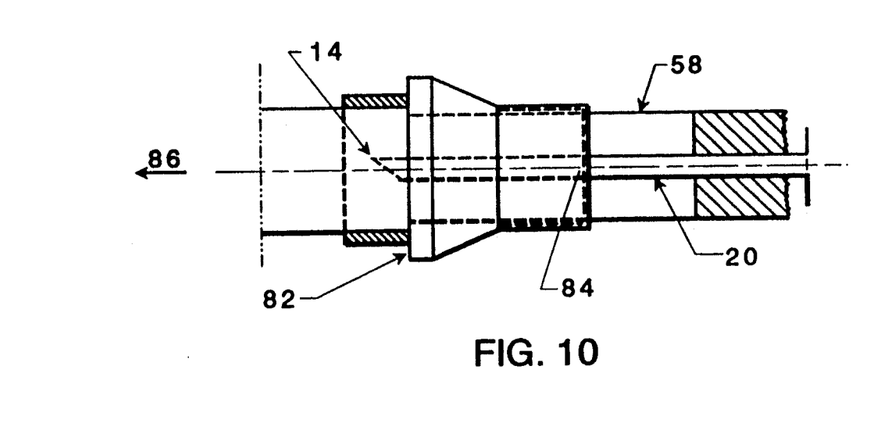
FIG. 10 shows the relative condition of the retaining member and the conduit after insertion of the conduit into the connector body.

FIG. 10 shows that after insertion, connector edge 40 and stop member edge 82 abut and press firmly against each other so that conduit 38 is held securely in placed and locked in primary body 12. A fluid leak seal has simultaneously been formed at 84 where diaphragm 46 encircles tubular structure 20.

Figure 5:
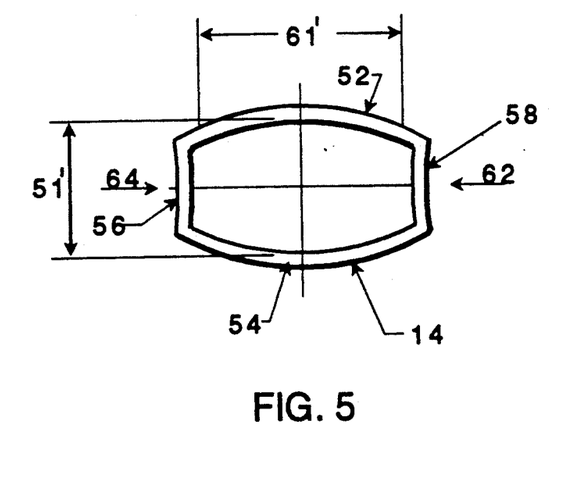
FIG. 5 illustrates movement of connector walls upon application of external forces.

To disconnect or unlock conduit 38 from connector 10, forces 64 and 62, such as are shown in FIGS. 4-5, are again applied to walls 56 and 58, respectively, causing walls 52 and 54 to move outwardly so that an interwall separation distance 51' is again achieved. Conduit 38 is now pulled in a direction 86, opposite to direction 78, and the conduit is now able to pass through flexible retaining end portion 14 and is released.

Figure 11:
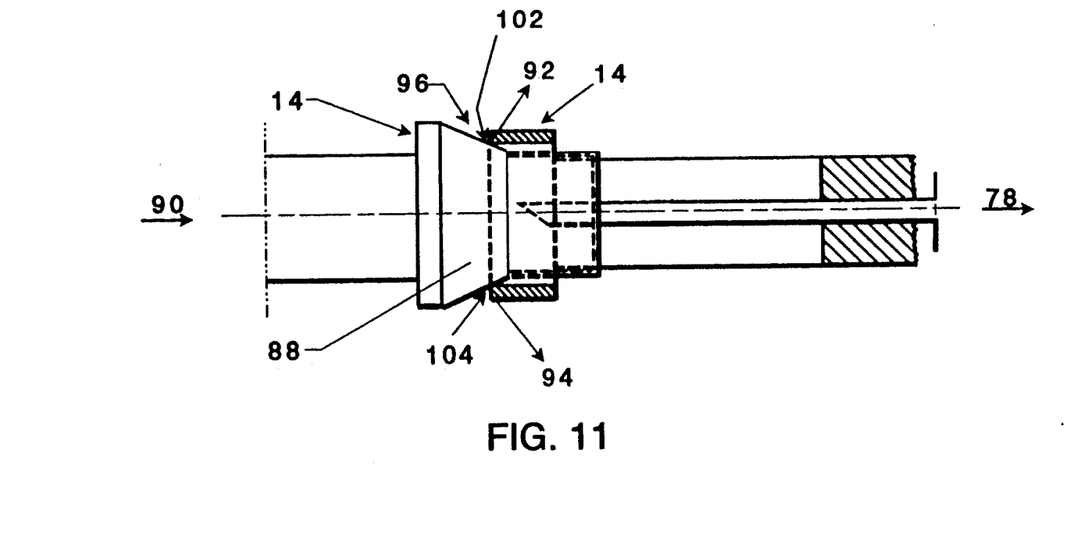
FIG. 11 shows an alternative embodiment of the connector eliminating the need for application of a force perpendicular to the sides to be applied in making the connection.

As a fourth embodiment, FIG. 11 further illustrates stop member 42 on conduit 38 as having a conical-shaped leading edge 88, as was also indicated in the connector of FIG. 8. In this case, it is not necessary to apply forces 62 and 64 during insertion of the conduit into the primary body. When conduit 38 is moved by a force 90 exerted in a direction 78 by the individual or entity making the connection/disconnection, secondary forces 92 and 94 are created by the interaction of surface 96 of inclined conical portion 88 of the stop member with leading edges 102 and 104 of walls 52 and 54, respectively. Forces 92 and 94 cause walls 52 and 54, respectively, to move outwardly sufficient distances so as to create an interwall separation distance 51' adequate to permit passage of stop member 42 beyond edge 40.

Conduit 38 is thus locked into primary body 12 without the need to apply perpendicular external forces 62, 64 to the side walls. The user is fully protected by the structure from being pricked by the needle providing the fluid conduit. The locking connection together with the activation of fluid delivery are essentially effectuated in a simultaneous manner simply by pressing together the conduit and the primary body.

In another alternative embodiment, the connector of the invention is used in a system whereby various medical components are interconnected by means of the double-male connector of primary body 12 (FIG. 2) to interconnect components, such as fluid bags, syringes, and IV tubing, that are already adapted with conduit 38 as the female counterpart of primary body 12, which together make the desired connection. Referring to FIG. 12, where like numerals are used in identifying components previously described, an assembly of various medical components as typically found in a medical operation procedure is illustrated. A fluid bag 201 has two fluid outlets, each terminated with a conduit 38 as part of the fluid bag. Two syringes 203 and 205 are depicted, along with fluid prescription bottle 207, IV tubing 209 and an intravenous needle, catheter 211 as would be inserted into a body, for example. All described components are affixed with a conduit 38 at their end portions, as indicated. Connection of the various components to one another is made quickly, and with a separation of the fluid flow from the mechanical locking mechanism of the connector, by means of primary body 12. For example, syringe 205 is connected to prescription bottle 207 to receive prescription fluid. The primary body 12 making that connection is then removed and discarded, and a new primary body 12 is used to make the connection of syringe 205 to the IV tubing for injection of the prescription fluid through intravenous needle 211 and into the body. The exact reverse operation would apply in removing body fluids, where a syringe is filled with fluid passing through the IV tubing, the primary body connector 12 is then removed and discarded, with a new primary body 12 attached to the syringe for injection of the fluid into a container, such as a test tube or storage body.

Exemplary applications of such a universal connector system are in the medical fields involving urinary analysis, and operations or other medical procedures involving gastric-jejunal, colon-rectal and surgical drain procedures.

Figure 13:
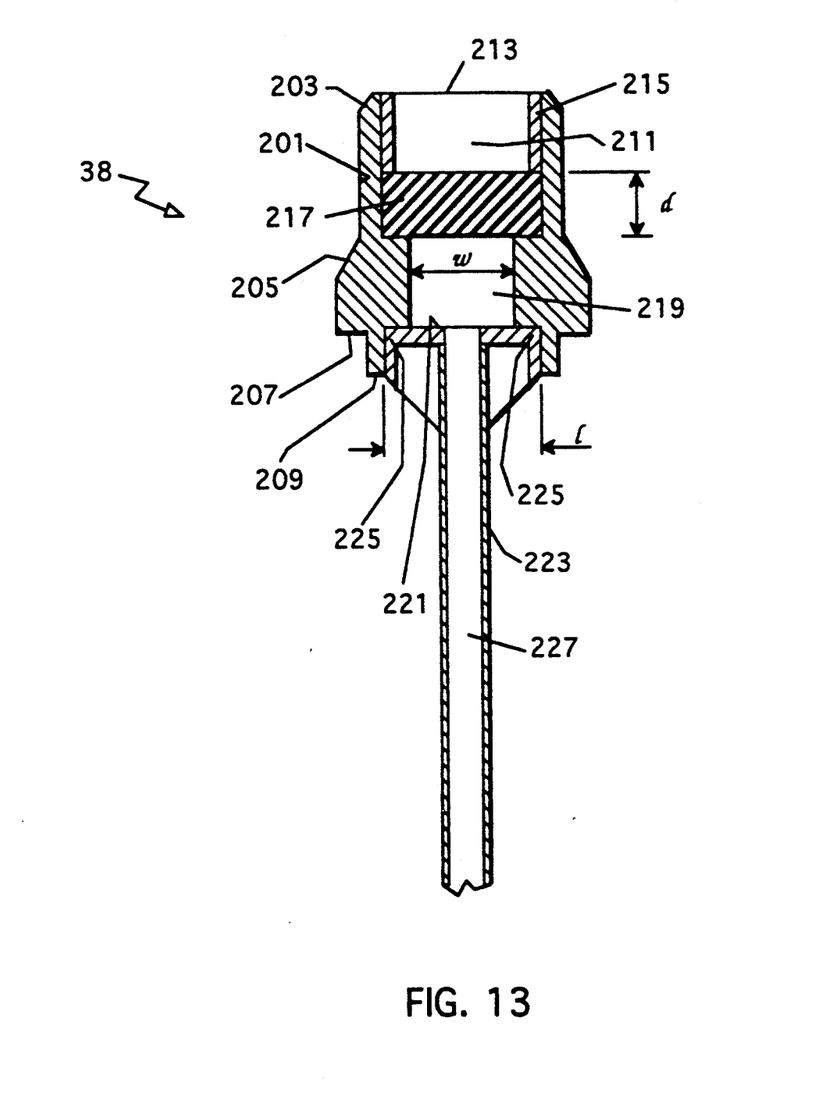
FIG. 13 illustrates an alternative embodiment of conduit 38.

In an alternate structure, conduit 38 as the female component of the connector of FIG. 1 comprises the more specific structure as shown in FIG. 13. Conduit 38 comprises a cammed body 201 having a cammed leading surface 203 and a cammed side surface 205, with a shoulder 207 at its base, from which extend projections 209. The top inner part of cammed body 201 is open, forming a recessed area 211 defined by the top edge 213 of the inner wall of cammed body 201. Positioned around the inner wall is a ring 215 securing against the side a latex disc 217 that forms the bottom of open area 211 and is puncturable by a sharply pointed object, such as tubular structure 20 of the connector's primary body 12. The latex disc is of a suitable thickness d for serving to secure fluids, and capable of being punctured at the same time providing a secure fluid seal, as is already known in the art. Beneath latex disc 217 is an open chamber 219, an area defined on the sides by lower inner walls of cammed body 201, on the top by the latex disc and on the bottom by the top flat surface 221 of a T-shaped member 223. The two arms 225 of the T-shaped member abut with projections 209 of the cammed body, are connected to one another by means of a fluid conduit 227, with a tapered surface extending downward from the projection 209 to the outer surface of fluid conduit 227.

In the conduit 38 as described, no sideward pressure is required on primary body 12 to make the connection. Rather, leading cammed surface 203 makes initial contact with flexible retaining end portion 14, which is followed by that same end portion coming in contact with cammed surface 205, thereby causing the slight movement of the end portion necessary for receipt of conduit 38. Once the conduit is engaged sufficiently far so that shoulder area 207 passes the internal flat surface 40 of end portion 14, the flexible end portion is relieved of the pressures exerted by the cammed surfaces of the conduit, and returns to its original shape, now securely held against removal by the action of inner flat surface 40 against shoulder 207 of the conduit.

At the same time, tubular structure 20 enters recessed are 211 and proceeds to puncture latex disc 217 and enter into chamber area 219 for either receipt or delivery of a fluid. By the same token, fluid conduit 227 having one end terminating at an opposite side of chamber are 219 is there also for either receiving or delivering a fluid. The junction between projection 209 and upper arms 225 is formed by either being glued, welded, or pressure fitted. The distance or length, 1, between the outer surfaces of the two arms 225 is a constant diameter, i.e. a fixed distance. The diameter of fluid conduit 227, on the other hand, is variable, up to a width, w, being the diameter of chamber area 219. Also, the structure as described around latex disc 217 allows for conduit 38 being used with tubular structures of a male component connector of also a variable diameter. Thus the flow is controllable in either direction, while at the same time giving a fully encircled protection, when used with a male counterpart of the connector, to the user from the internal needle structure and providing a quick connect mechanism totally separate from the fluid flow.

To release the connector, sideways finger pressure is exerted, as previously described, on the flexible retaining end portion 14 of the connector's primary body 12.

In the embodiment of FIG. 12 disclosing use of the connector in a universal connector system, conduit 38 of FIG. 13 is prepared by the manufacturer as the fluid port on any of the components shown, and is manufactured as part of the component, be it a fluid bag, a syringe, a prescription bottle or IV tubing. The double male connector of FIG. 2 could be carried, for example, in the pockets of the health care worker and immediately used on sight to conveniently and quickly make any connection desirable among the various system components.

The terms and expressions which have been employed in the foregoing abstract and specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A quick connect fluid coupling assembly, said assembly comprising:
    a body defined by an elongated channel centrally disposed along a longitudinal axis, wherein the body comprises a non-flexible central portion, a flexible retaining portion, and a connecting portion connecting said non-flexible portion and said flexible portion;
    a needle member disposed within said elongated channel and extending coaxially therewith, said needle member being attached to the non-flexible portion of the body, wherein a sharp-tipped end of said needle member terminates within the elongated channel; and
    a conduit means comprising an open end and a diaphragm covering the open end, wherein the conduit means is removably disposed within said elongated channel such that a fluid-tight seal is effected between the diaphragm and the needle member;
    wherein said flexible portion of the body comprises an elliptically shaped receiving means for receiving said conduit means, said elliptically shaped receiving means for holding said conduit means and being changeable to a more circular shape for inserting and removing said conduit means upon application of a force applied to the elliptically shaped receiving means.

2. An assembly as claimed in claim 1 wherein a distal end of said conduit means comprises connecting means for connecting said conduit means to a fluid source.

3. An assembly as claimed in claim 1, wherein said flexible portion comprises a ring integrally connected with said connecting portion.

4. An assembly as claimed in claim 1, wherein said connecting portion comprises two flexible longitudinally extending sections positioned opposite to one another, each of said two longitudinally extending sections having a first end integrally connected to said central portion and a second end integrally attached to said flexible portion.

5. An assembly as claimed in claim 2, wherein said connecting means comprises a T-connector attachment.

6. An assembly as claimed in claim 2, wherein said connecting means comprises a Y-connector attachment.

7. An assembly as in claimed in claim 2, wherein said connecting means is in fluid connection with a syringe.

8. A quick connect fluid coupling assembly, comprising:

a body comprising a rigid central portion, a flexible retaining portion comprising stop means, and a connecting portion integrally joining said rigid central portion and said flexible portion to form a centrally disposed elongated channel extending longitudinally through said body;

a cylindrically shaped needle member disposed within said elongated channel and extending longitudinally through said body, said needle member comprising a first end integrally attached to said rigid central portion, and an opposite sharp-tipped end extending longitudinally outward from said rigid potion and terminating within said flexible portion of said body;

a conduit means removably insertable through said flexible retaining portion into said centrally disposed elongated channel, said conduit means comprising an end wall surface on which is disposed a diaphragm for forming a fluid-tight sealing engagement with said needle member when said conduit is inserted into said elongated channel; and locking means for locking the conduit means in the elongated channel by engagement of said conduit with said stop means;

wherein said flexible portion of the body comprises an elliptically shaped receiving means for receiving said conduit means, said elliptically shaped receiving means for holding said conduit means and being changeable to a more circular shape for inserting and removing said conduit means upon application of a force applied to the elliptically shaped receiving means.

9. A quick connect fluid coupling assembly, said assembly comprising:

a body comprising a non-flexible central portion, a flexible retaining portion, and a connecting portion integrally joining said non-flexible central portion and said flexible retaining portion to form a centrally disposed elongated channel extending longitudinally through said body; and a needle member disposed within said elongated channel and extending longitudinally through said body, said needle member being attached to the non-flexible portion of the body, wherein an end of said needle member terminates within the elongated channel;

wherein said flexible portion of the body comprises an elliptically shaped receiving means for receiving a conduit means, said elliptically shaped receiving means for holding said conduit means and being changeable to a more circular shape for inserting and removing said conduit means upon application of a force applied to the elliptically shaped receiving means.

10. The quick connect fluid coupling assembly of claim 9, wherein said flexible retaining portion comprises a locking means for locking a conduit means in the elongated channel.

11. The quick connect fluid coupling assembly of claim 9, wherein the body defined by the elongated channel comprises a guide means for guiding a conduit means into the elongated channel.

* * * * *